(12) United States Patent
Cowan et al.

(10) Patent No.: US 9,023,054 B2
(45) Date of Patent: *May 5, 2015

(54) SURGICAL RESECTION GUIDE

(71) Applicant: Depuy (Ireland), Cork (IE)

(72) Inventors: Dean Cowan, Leeds (GB); Duncan Young, Hebden Bridge (GB)

(73) Assignee: Depuy (Ireland), Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/252,041

(22) Filed: Apr. 14, 2014

(65) Prior Publication Data

US 2014/0222005 A1  Aug. 7, 2014

Related U.S. Application Data

(63) Continuation of application No. 13/063,203, filed as application No. PCT/GB2009/051072 on Aug. 27, 2009, now Pat. No. 8,715,288.

(30) Foreign Application Priority Data

Sep. 10, 2008  (GB) .................................. 0816550.8
Jan. 15, 2009  (GB) .................................. 0900581.0

(51) Int. Cl.
*A61B 17/17* (2006.01)
*A61B 17/15* (2006.01)

(52) U.S. Cl.
CPC ............ *A61B 17/17* (2013.01); *Y10T 74/18312* (2015.01); *A61B 17/157* (2013.01)

(58) Field of Classification Search
CPC .... A61B 17/154; A61B 17/157; A61B 17/15; A61B 17/17
USPC ........ 606/86 R, 87, 88, 90, 102, 403; 254/98, 254/103, 14; 74/567, 569, 107, 55, 56, 57, 74/58

See application file for complete search history.

(56) References Cited

U.S. PATENT DOCUMENTS 3,661,019 A  5/1972  Kacalek
4,535,642 A  8/1985  Ohmura
(Continued)

FOREIGN PATENT DOCUMENTS

FR  2714811 A1  7/1995
FR  2726458 A1  5/1996
(Continued)

*Primary Examiner* — Todd Manahan
*Assistant Examiner* — Marcela I Shirsat

(57) ABSTRACT

A surgical resection guide comprising: a housing (36); a stylus arm (38) extending through the housing (36) arranged such that when the housing (36) is coupled to the side of a bone, a tip of the stylus arm (38) is arranged to contact an end of a bone; and a linear adjustment mechanism. The linear adjustment mechanism comprises: a shaft (30) at least partially received within a bore extending through the housing (36) such that the shaft (30) can slide along its longitudinal axis relative to the housing (36), the shaft (30) incorporating a shaft tooth or groove (50); and a dial (44) rotatably coupled to the housing (36) and incorporating a helical dial groove or rib (48) defining a longitudinal axis offset from the longitudinal axis of the shaft (30). The shaft tooth or groove (50) engages the dial groove or rib (48) such that rotating the dial (44) relative to the housing (36) causes the shaft tooth or groove (50) to slide along the dial groove or rib (48) causing the shaft (30) to slide within the bore along its longitudinal axis. The housing (36) and the stylus arm (38) can rotate about the shaft (30) without causing the shaft (30) to slide within its bore along its longitudinal axis. A method of adjusting the surgical resection guide is also disclosed.

14 Claims, 5 Drawing Sheets

(56) References Cited

U.S. PATENT DOCUMENTS

| | | |
|---|---|---|
| 5,683,397 A | 11/1997 | Vendrely |
| 7,033,361 B2 | 4/2006 | Collazo |
| 7,682,362 B2 | 3/2010 | Dees, Jr. |
| 8,372,080 B2 | 2/2013 | May |
| 2003/0028196 A1 | 2/2003 | Bonutti |
| 2005/0149042 A1 | 7/2005 | Metzger |
| 2005/0187557 A1 | 8/2005 | Collazo |
| 2005/0187560 A1 | 8/2005 | Dietzel |
| 2006/0179979 A1 | 8/2006 | Dees |
| 2013/0053766 A1 | 2/2013 | Hollett |

FOREIGN PATENT DOCUMENTS

| | | |
|---|---|---|
| FR | 2776176 A1 | 9/1999 |
| GB | 933355 A | 8/1963 |
| GB | 1165380 A | 9/1969 |
| GB | 2398011 A | 8/2004 |
| JP | 2007075517 A | 3/2007 |
| WO | WO 2007007067 A3 | 8/2007 |

SURGICAL RESECTION GUIDE

This application is a continuation of U.S. Ser. No. 13/063,203 filed Mar. 10, 2011, now U.S. Pat. No. 8,715,288, which is the national stage filing under 35 USC 371 of international application PCT/GB2009/051072 filed on Aug. 27, 2009, which claims foreign priority of GB 0900581.0 filed Jan. 15, 2009, and GB 0816550.8 filed on Sep. 10, 2008.

BACKGROUND OF THE INVENTION

The present invention relates to a surgical resection guide. In particular, the present invention relates to a surgical resection guide incorporating a mechanism for adjusting the spacing between two components which are coupled together.

During a total knee replacement procedure it is necessary to resect the end of the tibia to prepare the end of the tibia for implantation of a tibial prosthesis component. It may be necessary to resect a significant amount of bone from the end of the tibia, for instance 10 mm of bone. It is necessary to ensure that the resection plane is accurately located. In particular, it is necessary to ensure that the resection plane is positioned along the longitudinal axis of the tibia at a predetermined distance from a reference point on the surface of the end of the tibia.

A tibial resection is typically performed by aligning a cutting tool with a plane of a cutting guide. The cutting tool may press against and slide along an exterior surface of the cutting guide or the cutting tool may pass through a cutting slot formed within the cutting guide. Before the resection can be performed, the cutting guide must be accurately positioned relative to the bone such that the cutting guide exterior surface or the cutting slot is aligned with the chosen resection plane. Once in position, the cutting guide may be temporarily pinned in position to ensure a stable platform during the resection.

In order to adjust the position of the cutting guide the cutting guide may be mounted upon a slide rail coupled to the patient's leg and aligned with the tibia. The position of the cutting guide may then be adjusted along the rail until it is determined that it is correctly aligned with the resection plane. In order to align the cutting guide with a required resection plane it is known to provide a tibial stylus which couples to the cutting guide to allow the position of the cutting guide to be set relative to the reference point on the end of the bone.

Referring to FIG. 1, this illustrates a known form of tibial stylus. The tibial stylus comprises a shaft 2 coupled to a foot 4. The foot 4 comprises two plates 6a, 6b which extend from opposite sides of the shaft 2. Each plate 6a, 6b may be inserted into the cutting slot formed within the cutting guide. The plates 6a, 6b extend from shaft 2 at offset positions along the longitudinal axis of the shaft 2. The offset of plates 6a, 6b allows the same tibial stylus to be used to adjust the position of the cutting guide relative to the reference point on the end of the stylus either when the resection is to be performed through the cutting slot or when is it to be performed by aligning the cutting tool with an exterior surface of the cutting guide, according to the preference of the surgeon. If the resection is to be performed by aligning the cutting tool with an exterior surface of the cutting guide closer to the end of the bone then the cutting slot then plate 6a should be inserted into the cutting slot. If the chosen surgical technique is for resection to be performed through the cutting slot then plate 6b should be inserted into the cutting guide. The difference in position between plates 6a, 6b along shaft 2 is equal to the distance on the cutting guide between the exterior surface of the cutting guide and the cutting slot.

The tibial stylus further comprises a housing 8 having a bore through which the shaft 2 can slide. The housing 8 may also rotate about the shaft 2. The tibial stylus further comprises a stylus arm 10 coupled to the housing 8 so that it can slide through the housing 8 along an axis transverse to the axis of the shaft 2. Preferably the axis of the stylus arm 10 is perpendicular to the axis of the shaft 2.

The shaft 2 further comprises a series of annular grooves 12 proximal to the foot 4. Coupled to the housing 8 is a lever arm 14. Lever arm 14 is pivotally mounted upon the housing 8 and is biased by spring 16 such that a lower tooth part of the lever arm 14 engages an annular groove 12. When the lever arm 14 bears against an annular groove 12 the engagement of the tooth part with the annular groove 12 limits the ability of the shaft 2 to slide through the housing 8. While it may prove possible to overcome the engagement of the lever arm 14 with groove 12 by applying a force to the housing while holding the foot in position, the engagement is sufficiently strong that this is unlikely to happen accidently during a surgical procedure and in any event would be apparent to the surgeon as the tooth part clicked into a new groove. The strength of the engagement between the lever arm 14 and groove 12 is dependent upon the respective shapes of the groove 12 and the tooth part and the depth of the groove. The lever arm 14 may be released from an annular groove 12 by squeezing the free end of the lever arm 14 towards the housing 8, thereby overcoming the force applied to the lever arm 14 by spring 16. The shaft 2 is then free to slide through the housing 8 until the free end of the lever arm 14 is released and engages a different groove 12.

The tip 18 of stylus arm 10 may thus be raised or lowered relative to the foot 4. The tip 18 may be located on the reference point on the end of the bone by rotating the housing, and thus the stylus arm 10, around the shaft 2 and by sliding the stylus arm 10 though the housing 8. By adjusting the spacing between the tip 18 and the foot 4 parallel to the axis of shaft 2, by raising and lowering housing 8 along shaft 2 as described above, the cutting guide may be positioned relative to the bone so that the bone may be resected at an appropriate point along the bone away from the reference point. The exact location of a required resection plane is dependent upon an individual patient's anatomy.

The tibial stylus illustrated in FIG. 1 is calibrated so that the offset along the bone from the reference point to the resection plane is indicated by a gauge 20 engraved on the housing 8. The shaft 2 includes a reference mark 22 which indicates the position on the gauge. Sliding motion of the shaft 2 through the housing 8 adjusts the offset between the reference point and the resection plane. Sliding motion of the shaft 2 is limited to predetermined increments, for instance 2 mm, which are equal to the distance between adjacent annular grooves 12 along the axis of the shaft 2.

The known tibial stylus illustrated in FIG. 1 suffers from the disadvantage that the size of the markings on the gauge 20 are necessarily small, even if the numbering is staggered on the gauge 20, for instance the numbering may be at most 2.5 mm high for annular grooves 12 around the shaft which are 2 mm wide. This can mean that the gauge 20 is hard to read.

A further limitation of the known tibial stylus is that in order to adjust the position of the housing 8 along shaft 2 the lever arm 14 must be squeezed against the housing 8 and then the housing 8 raised or lowered along the shaft 2. This raising and lowering requires the use of large motor groups for the surgeon (arms and shoulders to lift the housing) in order to control a fine movement, which can result in overshooting the required resection level.

BRIEF SUMMARY OF THE INVENTION

It is an object of embodiments of the present invention to obviate or mitigate one or more of the problems associated with the prior art, whether identified herein or elsewhere. In particular, it is an object of embodiments of the present invention to provide an improved surgical resection guide for adjusting the spacing between a housing and a foot coupled to a shaft that extends through the housing.

According to a first aspect of the present invention there is provided a surgical resection guide comprising: a housing; a stylus arm extending through the housing arranged such that when the housing is coupled to the side of a bone, a tip of the stylus arm is arranged to contact an end of a bone; and a linear adjustment mechanism comprising: a shaft at least partially received within a bore extending through the housing such that the shaft can slide along its longitudinal axis relative to the housing, the shaft incorporating a shaft tooth or groove; and a dial rotatably coupled to the housing and incorporating a helical dial groove or rib defining a longitudinal axis offset from the longitudinal axis of the shaft; wherein the shaft tooth or groove engages the dial groove or rib such that rotating the dial relative to the housing causes the shaft tooth or groove to slide along the dial groove or rib causing the shaft to slide within the bore along its longitudinal axis; and wherein the housing and the stylus arm can rotate about the shaft without causing the shaft to slide within its bore along its longitudinal axis.

An advantage of the first aspect of the present invention is that control of the linear adjustment mechanism requires only rotation of the dial, and not raising or lowering of a component, as is the case with certain embodiments of the prior art. Consequently, only small motor groups for the operator (fingers and thumb to rotate the dial) are required, which aids in fine control of the adjustment mechanism, increasing its accuracy and usability. A further advantage of the first aspect of the present invention is that a gauge, including numbering can be provided upon the dial, which advantageously allows larger numbering to be used than would be the case for a corresponding linear gauge positioned along the shaft. The stylus arm can rotate about the shaft without causing the shaft to slide within its bore along its longitudinal axis. This allows the end of the stylus to independently rotate across the tip of a bone, while the stylus arm is moved up and down by adjusting the linear adjustment mechanism, until the stylus tip contacts a selected point on the end of the bone.

Preferably the shaft comprises a shaft tooth and the dial comprises a helical groove. The tooth may comprise a disc shaped flange extending from the periphery of the shaft and arranged such that the shaft can rotate about its longitudinal axis independently of sliding of the tooth along the helical groove.

The helical groove may be formed in an exterior cylindrical surface of the dial. Alternatively, the dial may include a bore and the shaft is at least partially received within the bore, and wherein the helical groove is formed in a side wall of said bore.

The longitudinal axis of the shaft and the longitudinal axis defined by the helical groove may be parallel. The extent of sliding motion of the shaft along its longitudinal axis may be limited to the distance along the longitudinal axis defined by the helical groove between a first end of the helical groove and a second end of the helical groove.

The helical groove may extend around the dial through at most one revolution of the dial.

The dial may further comprise an annular groove extending around the dial, the linear adjustment mechanism further comprising at least one pin extending through the housing such that a side surface of the pin engages said annular groove preventing the dial from being withdrawn from the housing.

A portion of the dial exterior to the housing may be arranged to be manipulated to rotate the dial relative to the housing.

The housing may further comprise a slot extending through to the bore such that the tooth may be viewed through said slot.

The housing may include a gauge arranged so that the position of the tooth relative to the gauge is indicative of the sliding position of the shaft relative to the housing.

The dial may comprise markings spaced apart around the periphery of a portion of the dial external of the housing, the position of the shaft along its longitudinal axis being indicated by the dial markings relative to a predetermined point on the housing.

The housing may further comprise a detent arranged to limit rotational movement of the dial to increments of a predetermined size.

The stylus arm may be coupled to the housing such that it can slide through the housing along an axis transverse to the axis of the shaft.

The end of the shaft extending from the housing may be coupled to a foot arranged to couple to a cutting guide coupled to the bone, and wherein when the dial is rotated about the longitudinal axis of the helical groove the distance between the tip of the stylus arm and the foot along the longitudinal axis of the shaft is varied.

The shaft may be fixedly coupled to the foot such that when the foot is coupled to the cutting guide, rotating the housing about the shaft causes the tip of the stylus arm to track across the surface of the end of the bone.

The foot may comprise first and second plates extending from the shaft from opposite sides of the shaft and offset from one another along the longitudinal axis of the shaft.

The surgical resection guide may further comprise a torsional spring coupled to the housing, a first arm of the torsional spring being arranged to contact the stylus arm at a point between the tip of the stylus arm and the housing such that the tip of the stylus arm is biased away from the end of the bone.

A portion of the shaft may extend from the housing comprises a series of annular grooves spaced apart along the longitudinal axis of the shaft, a second arm of the torsional spring being arranged to engage an annular groove such that the tip of the stylus arm is biased away from the end of the bone.

The second arm of the torsional spring may be arranged such that when the dial is rotated about the longitudinal axis of the helical groove the second arm sequentially engages said annular grooves as the shaft slides along its longitudinal axis such that rotational movement of the dial is restricted to increments of a predetermined size.

According to a second aspect of the present invention there is provided a method of adjusting a surgical resection guide, the surgical resection guide comprising: a shaft arranged having a first end arranged to be coupled to a cutting guide for performing a resection of a bone and a second end incorporating a shaft tooth or groove; a housing having a bore in which the shaft is at least partially received; a dial rotatably coupled to the housing, the dial incorporating a helical groove or rib, the helical groove or rib defining a longitudinal axis offset from a longitudinal axis of the shaft and the shaft tooth or groove engaging the helical groove or rib; and a stylus arm coupled to the housing and having a tip extending away from the housing, wherein the housing and the stylus can rotate about the shaft without causing the shaft to slide within the bore along its longitudinal axis; the method comprising: rotating the dial about the longitudinal axis of the helical groove or rib such that the shaft tooth or groove slides along the helical groove or rib causing the shaft to slide relative to the dial along its longitudinal axis through the housing such that the tip of the stylus is raised or lowered to a predetermined level relative to the cutting guide such that the tip of the stylus arm can contact the a reference point on and end of a bone.

In one embodiment there is a linear adjustment mechanism comprising a shaft incorporating a shaft tooth or groove; and a rotatable component incorporating a helical groove or rib defining a longitudinal axis offset from a longitudinal axis of the shaft; wherein the shaft tooth or groove slidably engages the helical groove or rib such that rotating the rotatable component about the longitudinal axis of the helical groove or rib causes the shaft tooth or groove to slide along the helical groove or rib causing the shaft to slide relative to the rotatable component along its longitudinal axis.

BRIEF DESCRIPTION OF THE DRAWINGS

The present invention will now be described, by way of example only, with reference to the accompanying drawings, in which.

DEATILED DESCRIPTION OF THE INVENTION

Figure 1:
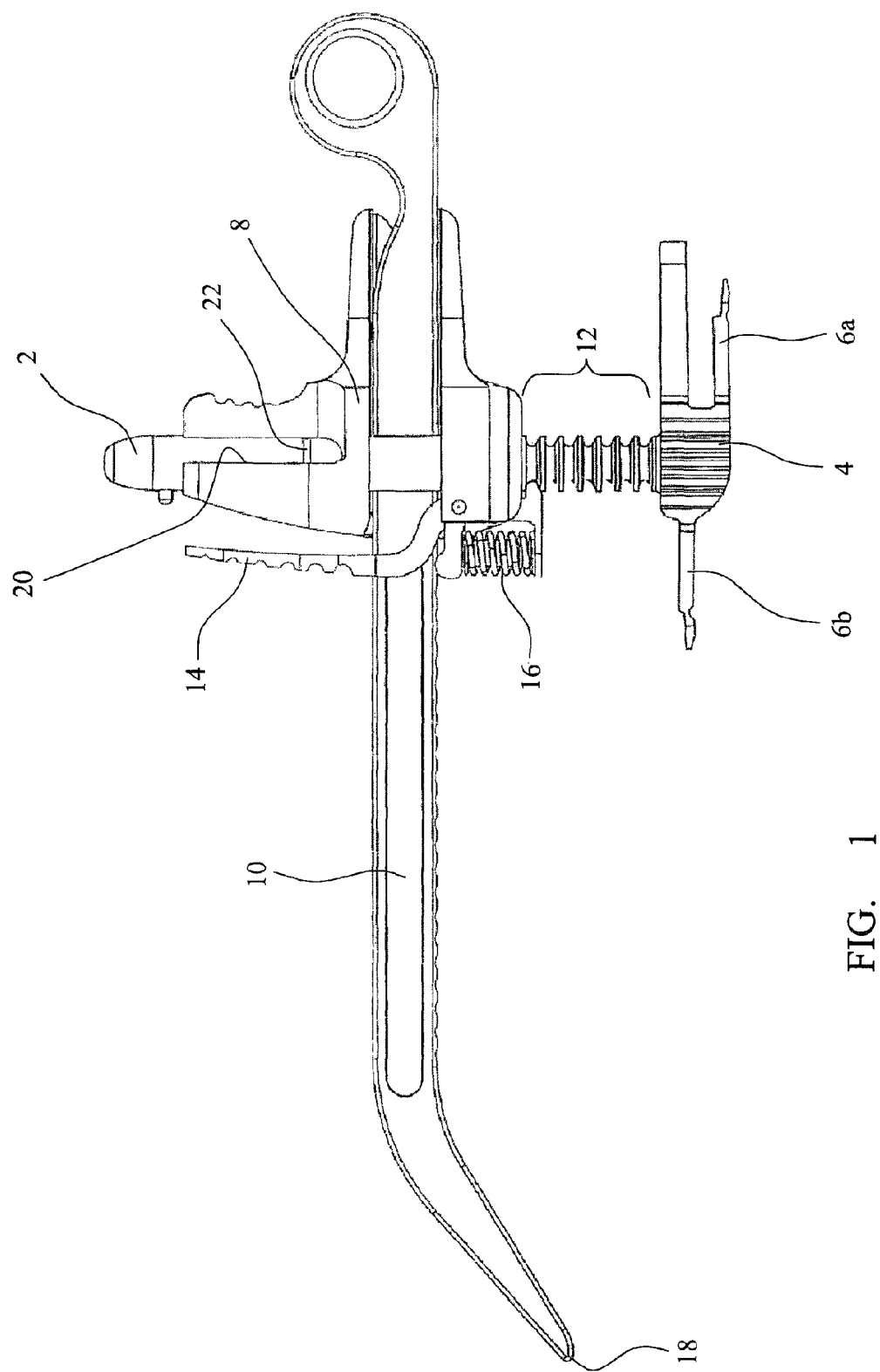
FIG. 1 illustrates a known tibial stylus.
Figure 2:
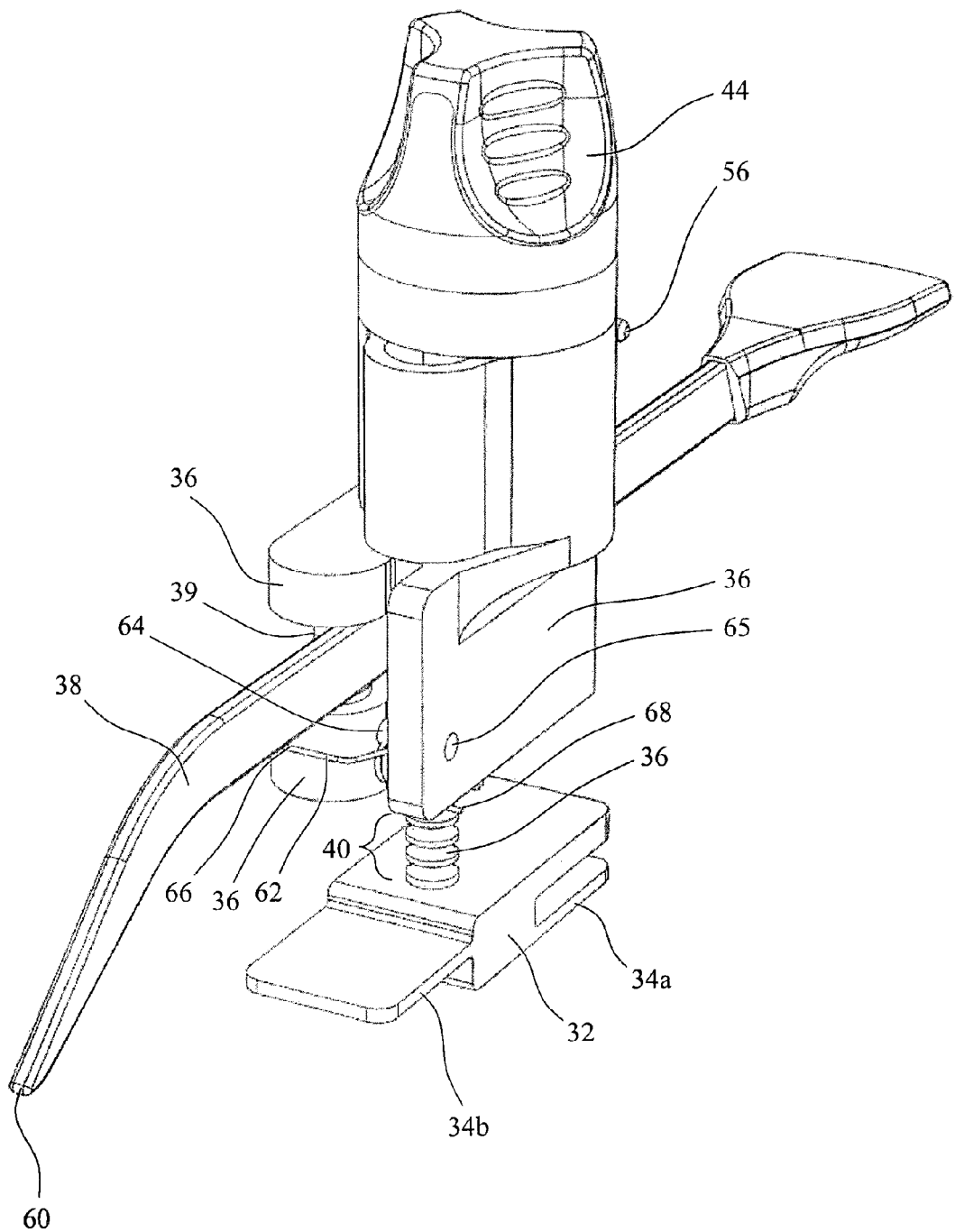
FIG. 2 illustrates a tibial stylus incorporating a linear adjustment mechanism in accordance with an embodiment of the present invention.

Referring now to FIG. 2, this illustrates a tibial stylus incorporating a linear adjustment mechanism in accordance with an embodiment of the present invention. The tibial stylus of FIG. 2 is generally similar to that of FIG. 1 except for the linear adjustment mechanism of the present invention replacing the adjustment mechanism of FIG. 1. Indeed the tibial stylus of FIG. 2 is intended to be used in a similar surgical procedure for the same purpose as that of FIG. 1.

The tibial stylus of FIG. 2 comprises a shaft 30 coupled to a foot 32. The foot 32 comprises two plates 34a, 34b which extend from opposite sides of the shaft 30. Each plate 34a, 34b may be inserted into a cutting slot formed within a tibial cutting guide. The plates 34a, 34b extend from shaft 30 at offset positions along the longitudinal axis of the shaft 30.

As for the tibial stylus of FIG. 1, the offset of plates 34a, 34b allows the same tibial stylus to be used to adjust the position of the cutting guide relative to the reference point on the end of the bone either when the resection is to be performed through the cutting slot or when is it to be performed by aligning a cutting tool with an exterior surface of the cutting guide, according to the preference of the surgeon. If the resection is to be performed by aligning the cutting tool with an exterior surface of the cutting guide closer to the end of the bone than the cutting slot then plate 34a should be inserted into the cutting slot. If the chosen surgical technique is for resection to be performed through the cutting slot then plate 34b should be inserted into the cutting guide. The difference in position between plates 34a, 34b along shaft 30 is equal to the distance on the cutting guide between the exterior cutting surface of the cutting guide and the cutting slot.

The tibial stylus further comprises a housing 36 having a bore through which the shaft 30 can slide. The housing 36 may also rotate about the shaft 30. The tibial stylus further comprises a stylus arm 38 coupled to the housing 36 so that it can slide through the housing 36 along an axis transverse to the axis of the shaft 30. Preferably the axis of the stylus arm 38 is perpendicular to the axis of the shaft 30. Stylus arm 38 is retained within the housing 36 by being trapped between a side wall of the housing 36 and pins 39 which pass through holes 41 within the housing 36. The stylus arm 38 can slide along its axis but is prevented from moving transverse to its axis out of the housing 36.

Figure 3:
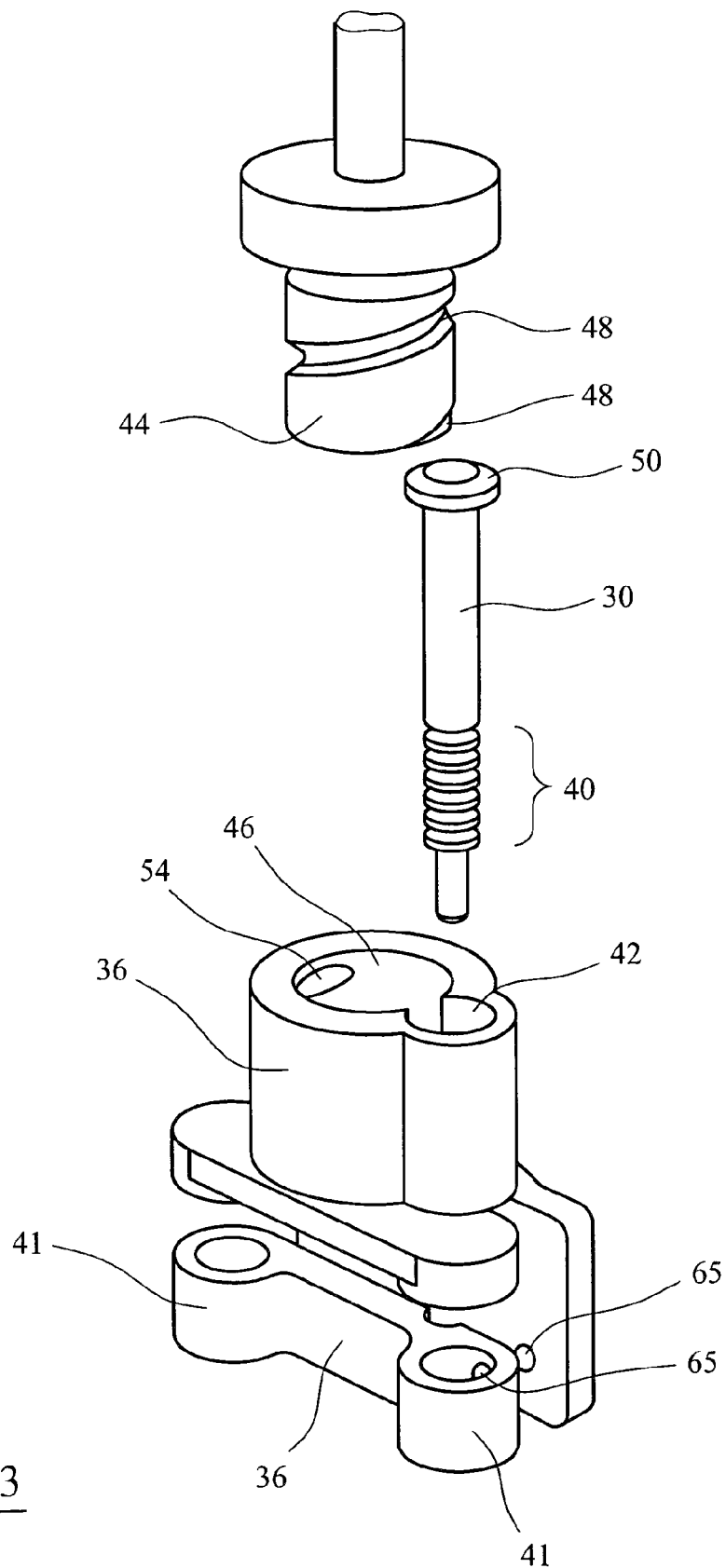
FIG. 3 illustrates an exploded view of the linear adjustment mechanism of FIG. 2.

Referring now also to FIG. 3, which illustrates in an exploded view the linear adjustment mechanism for the stylus of FIG. 2, the shaft 30 further comprises a series of annular grooves 40 in a lower portion of the shaft 30. It will be appreciated that to assemble the tibial stylus, the shaft 30 passes through bore 42 in housing 36 and the lower portion of the shaft 30 is coupled to foot 32. Annular grooves 40 are arranged to engage a spring mechanism which serves to bias the stylus arm 38 and the housing 36 relative to the shaft 30, as will be described below in greater detail below with reference to FIG. 5.

The linear adjustment mechanism further comprises a dial 44 which is received within a bore 46 within housing 36. The axis of bore 46 is offset from the axis of bore 42, and preferably parallel to the axis of bore 42. The dial 44 may, as illustrated, comprise an inner portion received within bore 46 and a cap portion fitting over the inner portion providing finger grips allowing a surgeon to rotate the dial 44 relative to the housing 36. Alternatively, the dial 44 may be provided as a single integral component.

Figure 4:
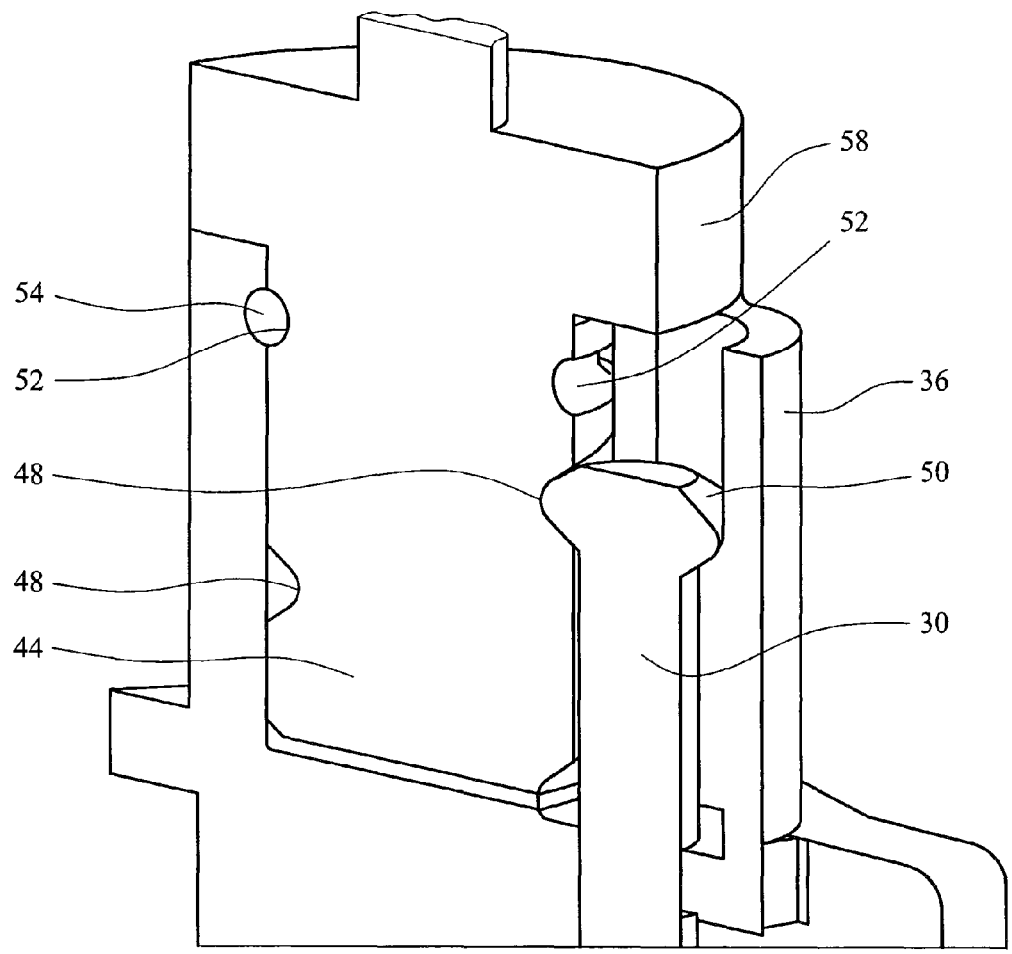
FIG. 4 illustrates a cross sectional view of the linear adjustment mechanism of FIG. 2.

The portion of dial 44 received within bore 46 is generally cylindrical. In an outer surface of the dial 44 there is provided a helical groove 48. Helical groove 48 extends around the dial 44 through approximately one full revolution of the dial 44. The two ends of helical groove 48 are offset along the longitudinal axis of the dial 44. Shaft 30 further comprises a tooth 50 in the form of a disc shaped flange at the end of the shaft 30 remote from the foot 32. Tooth 50 is arranged to engage the helical groove 48, as can be seen best in the cross sectional view of FIG. 4. Rotating the dial 44 relative to the housing 36 causes the tooth 50 to travel along the helical groove 48, until further rotation of the dial 44 is resisted by the tooth 50 reaching an end of the helical groove 48. It will be appreciated that the helical groove 48 may comprise either a left handed or a right handed helix, this affecting only the direction in which the dial must be turned in order to operate the linear adjustment mechanism.

Dial 44 further comprises an annular groove 52. Housing 36 further a bore 54 which passes through the housing 36 and intersects the side of bore 46. When dial 44 is fully inserted into bore 46, the annular groove 52 is aligned with the bore 54. A pin 56 may then pass through bore 54 and engage annular groove 52 thereby preventing the dial 44 from being retracted. As noted above, dial 44 has a generally cylindrical portion within bore 46. Adjacent to the cylindrical portion is a flange portion 58, which rests upon the upper surface of the housing 36.

As noted above, when dial 44 is rotated within bore 46, tooth 50 travels along the helical groove 48. As the dial 44 is prevented from moving out of bore 46, shaft 30 slides within bore 42 along its longitudinal axis. Consequently, rotating dial 44 causes the distance between the foot 32 and the housing 36 to vary. As the stylus arm 38 is coupled to the housing 36, the distance between the tip 60 of the stylus arm 38 and foot plates 34a, 34b may be varied.

During a tibial resection procedure a reference point on the surface of the end of the tibia is identified and a required distance between the reference point and the resection plane is chosen by the surgeon. The required distance is then set within the tibial stylus by rotating the dial 44 to adjust the distance between the stylus arm tip 60 and the foot 32. According to the chosen resection surgical technique (through the cutting slot or aligned with an exterior surface of the cutting guide, as described above) the appropriate foot plate 34a, 34b may be inserted into the cutting slot and the position of the cutting guide along the slide rail adjusted until the tip 60 touches the reference point.

Figure 5:
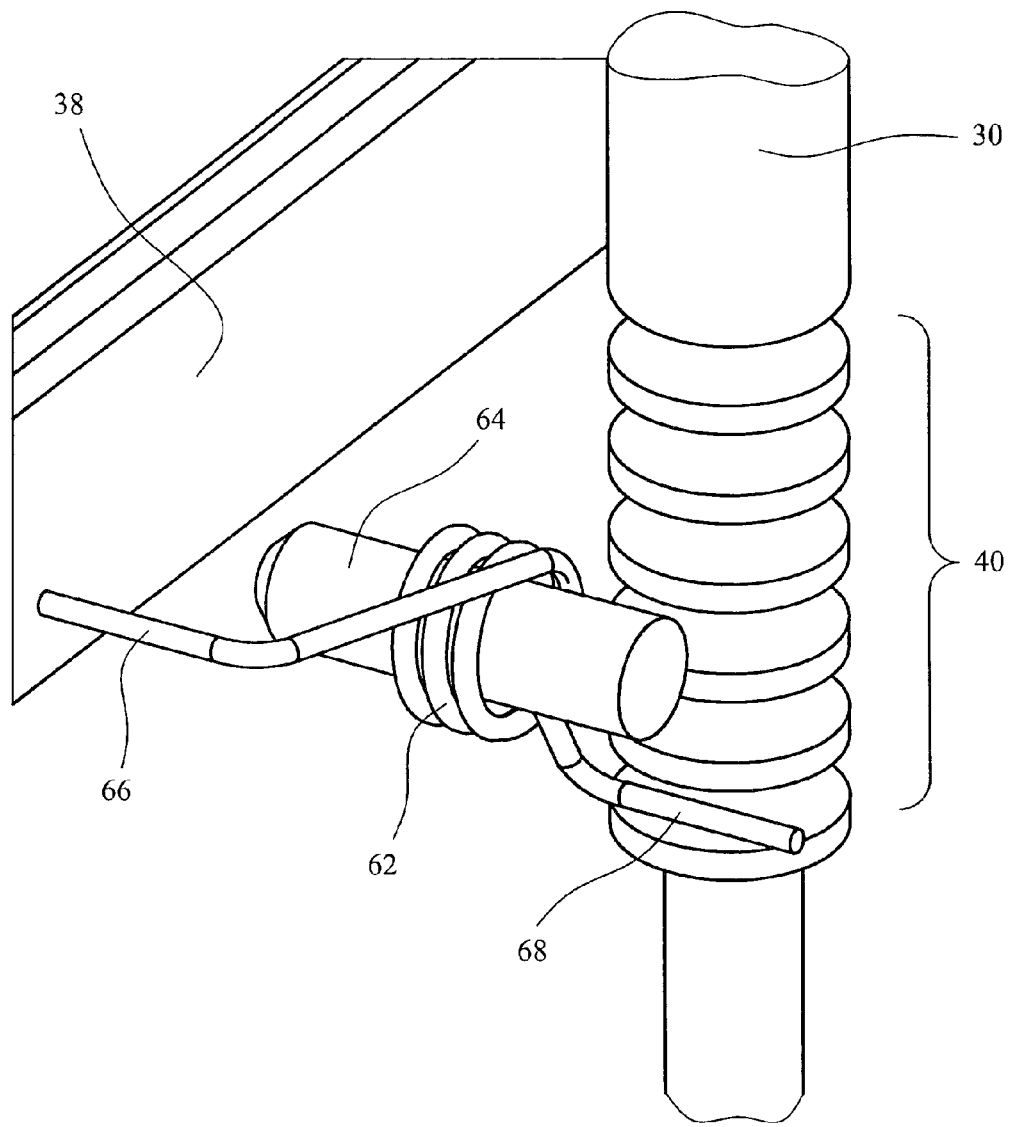
FIG. 5 illustrates a perspective view of part of the linear adjustment mechanism of FIG. 2.

Referring now to FIG. 5, the linear adjustment mechanism further comprises a spring mechanism arranged to bias the stylus arm 38 upwards (that is, in use such that the tip 60 is biased away from the end of the tibia). Furthermore, the spring mechanism is arranged to bias the housing 36 against the shaft 2, again with the effect that the stylus arm 38 is biased upwards. This is desirable to eliminate any play which is present within the stylus due to manufacturing tolerances in the couplings between the shaft 30, housing 36 and stylus arm 38.

The spring mechanism comprises a torsional spring 62 for which the wound portion is supported by a pin 64 which passes through a bore 65 within the housing 36. The torsional spring 62 has a first spring arm 66 extending upwards towards the stylus arm 38. Spring arm 66 bears against the stylus arm 38 biasing it upwards. In effect, the stylus arm 38 is twisted within the bore passing through the housing 36 such that if there is any slack within the bore the stylus arm 38 is pressed against one edge of the bore and is not free to move around. The underside of the stylus arm 38, against which the spring arm 66 bears may be provided within a series of grooves spaced apart along the length of the stylus arm 38. Advantageously, the engagement between the spring arm 66 and the grooves is such that the stylus arm 38 may slide through the housing 36 and be held in position by the spring arm 66 to prevent the stylus arm 38 from slipping. The stylus arm 38 may thus be adjusted in position relative to the housing 36 in discrete increments according to the spacing between the grooves.

The torsional spring 62 further comprises a second spring arm 68 extending towards shaft 30. Spring arm 68 bears against shaft 30 and engages one of the annular grooves 40 extending around shaft 30. In effect, the shaft 30 is twisted within bore 42 such that if there is any slack within bore 42 the shaft 30 is pressed against one edge of bore 42 and is not free to move around.

As dial 44 is rotated, shaft 30 slides within bore 42 and the point of contact between spring arm 68 and shaft 30 changes. Annular grooves 40 are shaped such that the spring arm 68 is encouraged to settle within a groove 40. Consequently, as dial 44 is rotated there will be a detectable variation in the force resisting rotation of the dial. Dial 44 effectively is rotatable only between predefined rotary positions corresponding to the spring arm 68 sequentially engaging each annular groove 40. The annular grooves 40 are regularly spaced apart along the shaft 30, for instance spaced apart by 2 mm. The effect is that by rotating the dial 44 the tip 60 may be raised or lowered in 2 mm increments. The number of annular grooves 40 and their spacing along shaft 30 is arranged such that when dial 44 is rotated sufficiently for tooth 50 to travel along the full length of helical groove 48 (which may correspond to one complete revolution of the dial 44) the tip 60 is raised or lowered throughout a predetermined distance corresponding to the maximum height adjustment of the linear adjustment mechanism. For instance, as illustrated in FIG. 5, there are six annular grooves 40, which may be spaced apart by 2 mm. As shaft 30 slides within the housing 36 the arm 68 may sequentially engage each of the neighbouring five annular grooves 40, corresponding to a total linear adjustment of 1 cm. The linear adjustment mechanism allows the distance between the reference point on the end of the tibia and the resection plane to be varied over a range of 1 cm (in addition to any fixed offset between tip 60 and foot 32 when the arm 68 engages the lowermost annular groove 40). A gauge may be provided on the outside visible surface of dial 44 such that the required linear offset can be selected by comparing the gauge to a reference point on the housing. Applying a force to the housing 36 while holding foot 32 stationary does not cause the shaft 30 to slide within bore 42 if the inclination of the helical groove relative to the longitudinal axis of the shaft 30 is sufficiently shallow. However, the linear adjustment mechanism may still be operated by applying minimal force to rotate the dial 44.

The above described linear adjustment mechanism couples the dial mechanism to the shaft tooth by providing a helical groove on the outside of a cylindrical portion of the dial. The helical groove defines a longitudinal axis which is offset from, but parallel to, the longitudinal axis of the shaft. In this embodiment, the longitudinal axis of the helical groove is coincident with the longitudinal axis of the dial itself. As the axis is offset from the axis of the shaft, rotation of the dial relative to the housing is unlikely to cause the housing to rotate. The greater the offset, the less rotational force about the shaft is transmitted to the housing when the dial is rotated. This assists with maintaining the tip of the stylus arm in position over the reference point on the end of the tibia as the linear adjustment mechanism is operated to raise or lower the tip.

In accordance with an alternative embodiment of the present invention, the dial may alternatively comprise a cylindrical component received in and rotatable within a bore in the housing, the dial itself having an interior bore within which and end of the shaft is received. The helical groove may be provided on a side wall of the dial bore such that the tooth at the end of the shaft within the bore into the dial engages the helical groove. The longitudinal axis of the shaft remains offset from the longitudinal axis of the helical groove, such that as the dial is rotated the shaft is raised or lowered within the bore in the base of the dial. Furthermore, as the axes are offset, rotating the housing around the shaft does not cause the shaft to slide along its axis. Advantageously, arranging the linear adjustment mechanism in this manner allows the offset between the shaft and the axis of the helical groove to be reduced while preserving the same pitch of the helical groove. Reducing the offset results in a smaller adjustment mechanism, and hence a smaller tibial stylus.

As noted above, the tooth comprises a disc shaped flange at one end of the shaft. Preferably the tooth is circular in cross section in a plane perpendicular to the longitudinal axis of the shaft such that as the housing rotates about the shaft the engagement between the helical groove and the tooth is unaffected. That is, the tooth extends from the shaft equally in all directions. Advantageously, this allows the housing to be rotated about the shaft, for instance by manipulating the stylus arm to turn the tibial stylus, without adjusting affecting the linear adjustment mechanism. The longitudinal axis of the helical coil and the shaft may be parallel to one another. However, in order to ensure that the tooth remains firmly engaged within the helical groove as the dial is rotated, the axes may be positioned at a slight angle to one another such that the dial bears against the tooth. The dial mechanism may also be flexible to ensure that contact is maintained with the tooth without making it too difficult to rotate the dial.

For the linear adjustment mechanism described above the helical groove extends around the dial by one complete revolution. Consequently, rotating the dial by one complete revolution causes the linear adjustment mechanism to travel through its complete linear range. It will be appreciated that the helical coil could complete more than one revolution around the dial, which would advantageously reduce the required pitch of the groove for a given height range and a given diameter of the dial. However, it would be difficult to be able to determine solely from a gauge on the outside of the dial what linear offset had been selected as the gauge would overlap itself. The helical groove may extend through less than one complete revolution of the dial; however this has the effect of increasing the required pitch of the helical groove to achieve the same linear adjustment range. In addition to the gauge on the outside of the dial (read against a reference mark upon the housing) the outside of the dial may also provide finger mouldings to make it easier to rotate.

In addition to the rotary gauge on the dial, a linear gauge may also be provided for determining the selected offset. A slot may be provided in the side of the housing extending through to the bore which receives the shaft allowing the shaft to be viewed. A gauge may be provided along the slot, and read by comparing the gauge with a reference point on the shaft, for instance the tooth.

As discussed above, the torsional spring serves to ensure that the rotational position of the dial is adjustable between discrete predetermined rotational positions, and consequently the position of the shaft along its longitudinal axis relative to the housing is restricted to one of a series of discrete predetermined linear positions. Alternatively, a detent may be provided within the bore in the housing which receives the dial to restrict the rotational position of the dial to discrete predetermined rotational positions. For instance the dial may comprise a peripheral series of teeth or grooves and the bore may comprise a flexible detent arranged to engage a tooth or a groove to restrain the rotational position of the dial. The detent may be overridden by applying a rotational force to the dial exceeding the force required to flex the detent to allow the detent to sequentially engage each tooth or groove.

As described above, the linear adjustment mechanism is dependent upon the tooth engaging the helical groove such that the tooth slides along the groove when the dial is rotated. The diameter of the helix is in inverse proportion to the pitch angle of the helix in order to achieve the same range of linear movement. As the pitch angle of the helix changes the shape of the tooth is optimised to ensure snug engagement.

The present invention has primarily been described in terms of a linear adjustment mechanism comprising a shaft incorporating a tooth and a dial or other form of rotatable component comprising a helical groove. However, it will be readily apparent to the appropriately skilled person that the linear adjustment mechanism may equally comprise a shaft incorporating a shaft groove (for instance, an annular groove extending entirely around the shaft) and a rotatable component comprising a helical rib arranged to slidingly engage the shaft groove. In other words, the cross sectional profiles of the tooth and groove are inverted.

Linear adjustment mechanisms in accordance with embodiments of the present invention described above have been primarily been associated with a tibial stylus. However, it will be appreciated that the linear adjustment mechanism may be more widely applicable. For instance, it may equally be applied to styluses used when resecting other bones, for instance a femur. Furthermore, the linear adjustment mechanism may applicable to other instruments, and in particular other surgical instruments, for instance for adjusting a depth stop for a drill. More generally, the present invention may be used in any application which requires fine control to be achieved other the relative position of two components. Further modifications to, and applications of, the present invention will be readily apparent to the appropriately skilled person from the teaching herein without departing from the scope of the appended claims.

The invention claimed is:

1. A surgical resection guide for use with a bone, comprising:
   a housing having a first bore having a first bore axis;
   a stylus arm having a tip, the stylus arm being connected to the housing such that, when the housing is coupled to the side of a bone, the tip is positionable to contact the bone;
   a shaft having a shaft longitudinal axis, the shaft at least partially received within the first bore such that the shaft can slide along the shaft longitudinal axis relative to the housing, a portion of the shaft extending from the housing comprising a series of annular grooves spaced apart along the shaft longitudinal axis; and
   a torsional spring coupled to the housing;
   wherein the torsional spring has a first spring arm that contacts the stylus arm at a point between the tip and the housing to bias the tip away from the end of the bone and a second spring arm that engages an annular groove of the series of annular grooves to press the shaft against an edge of the first bore.

2. The surgical resection guide of claim 1, wherein the stylus arm extends through the housing.

3. The surgical resection guide of claim 1, wherein the stylus arm is slidably coupled to the housing along an axis transverse to the shaft axis.

4. The surgical resection guide of claim 1, wherein the second spring arm sequentially engages one of the series of annular grooves followed by another of the series of annular grooves as the shaft slides along the shaft longitudinal axis so as to restrict rotational movement of the dial to increments of a predetermined size.

5. The surgical resection guide of claim 1, further comprising:
   a dial having a dial longitudinal axis, the dial rotatably coupled to the housing and having a dial groove or rib;
   wherein the shaft includes a shaft tooth or shaft groove that engages the dial groove or rib, respectively, such that, when the dial is rotated relative to the housing from a first angular position to a second angular position, the shaft tooth or shaft groove slides along the dial groove or rib causing the shaft to move from a first position to a second position along the dial longitudinal axis; and
   wherein when the dial is rotated about the dial longitudinal axis the second spring arm sequentially engages one of the series of annular grooves followed by another of the series of annular grooves as the shaft slides along the shaft longitudinal axis so as to restrict rotational movement of the dial to increments of a predetermined size.

6. The surgical resection guide of claim 5, wherein the shaft comprises a shaft tooth formed as a disc shaped flange extending from the periphery of the shaft, and the dial groove is a helical groove.

7. The surgical resection guide of claim 6, wherein the dial has a cylindrical portion having a cylindrical surface, the helical groove being formed in the cylindrical surface.

8. The surgical resection guide of claim 5, wherein the dial includes a side wall, the helical groove is formed in the side wall, and the shaft tooth is at least partially received within the helical groove.

9. The surgical resection guide of claim 5 wherein the dial groove extends around the dial through at most one revolution of the dial.

10. The surgical resection guide of claim 5, wherein the dial longitudinal axis is offset from the shaft longitudinal axis.

11. The surgical resection guide of claim 10, wherein the shaft longitudinal axis and the dial longitudinal axis are parallel.

12. The surgical resection guide of claim 5, wherein the dial comprises markings spaced apart around the periphery of a portion of the dial external of the housing, the position of the shaft along the shaft longitudinal axis being indicated by the dial markings relative to a predetermined point on the housing.

13. The surgical resection guide of claim 5, wherein an end of the shaft extending from the housing is coupled to a foot arranged to couple to a cutting guide coupled to the bone such that, when the dial is rotated about the dial longitudinal axis the distance between the tip of the stylus arm and the foot along the longitudinal axis of the shaft is varied.

14. The surgical resection guide of claim 13, wherein the shaft is fixedly coupled to the foot such that when the foot is coupled to the cutting guide, rotating the housing about the shaft causes the tip of the stylus arm to track across the surface of the end of the bone.

\* \* \* \* \*